United States Patent [19]

Ortueta Corona

[11] Patent Number: 4,815,835
[45] Date of Patent: Mar. 28, 1989

[54] OPTICAL APPARATUS WITH A SLIDE LIGHTING SYSTEM FOR DETECTING A WOMAN'S FERTILE PERIOD DURING HER MENSTRUAL CYCLE

[76] Inventor: Luis F. Ortueta Corona, San Ramón Nonato, 1 - 7°A, 28046 Madrid, Spain

[21] Appl. No.: 48,769

[22] Filed: May 12, 1987

[30] Foreign Application Priority Data

May 16, 1986 [ES] Spain .................................. 294191

[51] Int. Cl.$^4$ .............................................. G02B 21/00
[52] U.S. Cl. .................................... 350/507; 128/738; 350/518; 350/523
[58] Field of Search ............... 350/507, 521, 523, 529, 350/235–238; 128/738

[56] References Cited

U.S. PATENT DOCUMENTS

| | | | |
|---|---|---|---|
| 2,808,761 | 10/1957 | De Grave, Jr. ...................... | 350/235 |
| 3,037,496 | 6/1962 | Melges ................................. | 128/738 |
| 3,582,181 | 6/1971 | de Chveca ........................... | 350/518 |
| 4,361,377 | 11/1982 | Pullen ................................. | 350/523 |
| 4,534,362 | 8/1985 | Schumacher et al. .............. | 128/738 |

FOREIGN PATENT DOCUMENTS 813405 5/1959 United Kingdom .

Primary Examiner—John K. Corbin
Assistant Examiner—Martin Lerner
Attorney, Agent, or Firm—Ladas & Parry

[57] ABSTRACT

An optical apparatus with a slide lighting system for detecting a fertile period during a woman's menstruation cycle from her saliva has inner and outer telescopic tubular bodies. The inner tubular body has an optical system of three, fixed lenses for 100 fold magnification of the saliva on a slide. The outer tubular body has, at one free end, a window for receiving the slide and threading for the axial attachment of another light-device tubular body for lighting the slide.

1 Claim, 3 Drawing Sheets

OPTICAL APPARATUS WITH A SLIDE LIGHTING SYSTEM FOR DETECTING A WOMAN'S FERTILE PERIOD DURING HER MENSTRUAL CYCLE

The present invention relates to an optical apparatus with a slide lighting system for the detection of a woman's fertile period during her menstrual cycle.

BACKGROUND OF THE INVENTION

As known, a woman's menstrual cycle lasts about four weeks and there are more than enough reasons to suppose that her human ovule can be fertilized at any time within 12 hours following its ovulation. In its ovulation, the ovule is ejected out of the ovary and begins to migrate inside the feminine genital organs. If, during the 12-hour time interval, the ovule has not been reached by a spermatozoon, it will be destroyed.

Despite the fact that the mechanism of menstruation is respetitive and commonly known as a period, it appears irregularly most times. A cycle lasts, in general, from 27 to 30 days, while menstruation lasts from 3 to 7 days in the cycle. At least the variation in the cycle duration may be due to climatological and psychic influences.

The point where the ovule and the spermatozoon generally meet is the lower third of the feminine genital duct. During ejaculation, the seminal fluid enters the back portion of the vagina and the spermatozoon in the seminal fluid then begin to migrate upwards along the mucous membrana coating the duct. During this migration of from 15 to 20 cm to the ovaries, most of the spermatozoon die. Those which are stronger may meet and fertilize a live ovule. The rest continue migrating until their complete exhaustion, being finally phagocyted by white cells. The spermatozoon maintain their fertilizing capability for about 30 hours, at most, even though they move inside a woman's womb for about 48 hours.

Because the spermatozoon and ovule have very short lives, 30 hours and 12 hours, respectively, after being ejaculated and ejected from the ovary, and the time of such ovary ejection is variable, the possibility of such fertilization within a menstrual cycle is limited. It only exists from just before (18 hours) to immediately after (12 hours) ovulation, which takes place approximately at the midpoint of the cycle, between 17 and 12 days before the next menstruation, thereby defining fertile and sterile periods in the menstrual cycle.

As long ago as 1976, well-reputed scientists from the Universities of Ontario, in Canada, Haifa, in Israel, and Auckland, in New Zealand, announced researches carried out on women's saliva during their menstrual cycles. They observed a clear difference in the cell pattern in saliva between fertile and sterile periods. Since then, a great number of scientists at other universities of the world joined in the aforementioned researches, also finding a clear difference in women's saliva between fertile and sterile periods, and possibly detecting diseases and irregularities in the gynaecological system as well. At least 153 scientists at 41 universities from 1976 to 1985 have verified this fertility indicating system. Their researches have, up to now, always been carried out in the laboratory, however.

This research shows that saliva crystallization appears when the blood folliculin level has reached a certain height that coincides with the third or fourth day before ovulation. The crystallization lasts until 3 or 4 days after ovulation, when the presence of lutein inhibits the crystallization. Due to this, the crystallization even indicates fertile period, since it takes place from 3 or 4 days before ovulation up to 3 or 4 days after it.

As a matter of information, a list of researches carried out in 1985 concerning this subject is detailed hereinafter:

Drs. Tho, S. P., Scholer, J., Phung, B. V., Harp, R. J., and McDnough, P. G., "Radioimmunoassay of progesterone in saliva: a simplified technique using 125I-radioligand." Dep. of Obstetrics and Gynaecology, Medical College of Georgia, Augusta, Ga., UNITED STATES.

Drs. Campbell, W. G., Priest, R. E., and Weathers D. R., "Characterization of two of crystalloids in pleomorphic adenomas of minor salivary glands. A light microscopic," Dept. of Pathology, Emory University School of Medicine, Atlanta, Ga., UNITED STATES.

Drs. Belkien, L. D., Bordt J., Moeller P., Hano R., and Nieschiag E., "Estradiol in saliva for monitoring follicular stimulation in an in vitro fertilization program," Max Planck Clinical Research Unit for Reproductive Medicine, Muenster, FEDERAL REPUBLIC OF GERMANY.

Drs. Walker, R. F., Wilson, D. W., Truran, P. L., Read, G. F., and Richards, C. "Characterization of profiles of salivary progesterone concentrations during the luteal phase of fertile and subfertile women," Tenovus Institute for Cancer Research, Welsh National School of Medicine, The Heath Cardiff, WALES.

Drs. Read, G. F., Bradely, J. A., Wilson, D. W., and Griffiths, K., "Evaluation of luteal-phase salivary progesterone levels in women with benign breast disease or primary breast cancer," Tenevous Institute for Cancer Research, Welsh National School of Medicine, Heath Park, Cardiff, WALES.

Drs. Sulfi, S. B., Donaldson, A., Gandy, S. C., Jeffcoste, S. L., and Chearskul, S., "Multicenter evaluation of assays for estradiol and progesterone in saliva," WHO Collaborating Centre, Chelsea Hospital for Women, London, ENGLAND.

Drs. Cedar, L., Nathan, C. Janssens, Y., Savale, M., and Guichard, A., "Salivary progesterone profile after in-vitro," ENGLAND.

As indicated above, the detection of a woman's fertile period during her menstrual cycle on the basis of the change in the structure of her saliva has only been carried out in the laboratory, which leads to a great difficulty in the determination of the salivary activity at an adequate moment and place in each cycle. The woman cannot make an auto-analysis and, thus, know her fertility period at any given moment.

SUMMARY OF THE INVENTION

An object of the invention is to enable a woman to detect her menstrual cycle continually through salivary auto-analysis, in a clean and comfortable way, detecting likewise irregularities or diseases which might appear in the gynaecological system, this being quite in accordance with current public health and preventive medicine programs.

Another object of the invention, in accordance with the philosophy that characterizes the most modern mentality in the population and without pharmacological intervention, is birth control or, on the contrary, indication of the short, fertile period four days beforehand.

Another object is to provide an optical apparatus for the foregoing objects that is easy to handle, small and available at a popular price, within the reach of all home economies and with the advantages in the auto-analysis.

Another object is to provide birth control/fertility indication without the need to consume any product.

Another object is to provide the above without the need to know how to handle electronic devices, the optical apparatus according to the invention being really simple to use, it only being necessary for a woman to lay some saliva drops on a slide and then observe through the apparatus whether she is fertile or not, the observed detection being available at that moment.

The optical apparatus according to the invention is, in general, constituted by two telescopic tubular bodies, the inner one of which has a set of magnifying lenses with a focusing adequate for its purpose, the total magnification of said lenses being, preferably, 100 times. The inner tubular body can be easily moved axially with respect to the outer tube in order to focus on a slide which is diametrically located in the outer tubular body through a window provided to that effect.

The main characteristic of the invention lies in the fact that said outer tubular body has at its free, mouth end, a lighting device in another tubular body having a bottom at one end and threading connection to the mouth of the outer tubular body at the opposite end. The lighting device has a battery, preferably of 1.5 V, which feeds a bulb of identical voltage via an electric circuit opened or closed by a switch emerging from the outside of the other tubular body.

BRIEF DESCRIPTION OF THE DRAWINGS

For better comprehension of the invention, a series of drawings is attached in which, in an illustrative and non-limitative character, the following has been represented.

DESCRIPTION OF THE PREFERRED EMBODIMENT

Figure 1:
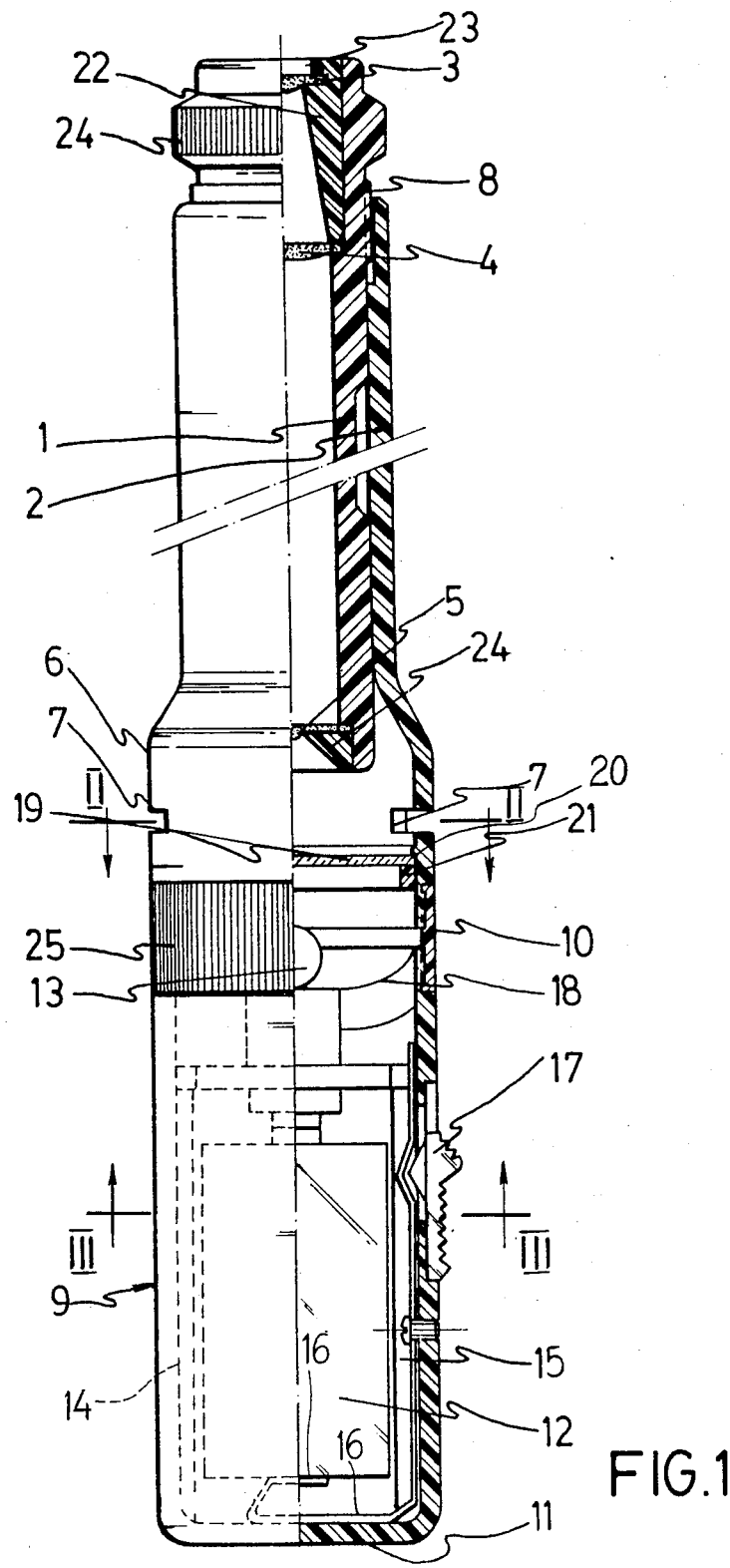
FIG. 1 is a longitudinal, quarter-sectioned elevation, partly broken away, of an optical apparatus with slide lighting system according to the invention.

With reference to the reference characters indicated in the Figures, an optical apparatus with slide lighting system for detection of a woman's fertile period during her menstrual cycle according to the invention has, in the preferred embodiment shown, inner and outer telescopic tubular bodies 1 and 2, respectively. The inner tubular body 1 supports a lens system formed by magnifying lenses 3, 4 and 5, which are fixed at distances therealong so as to produce a preferred total magnification of 100 times.

Figure 2:
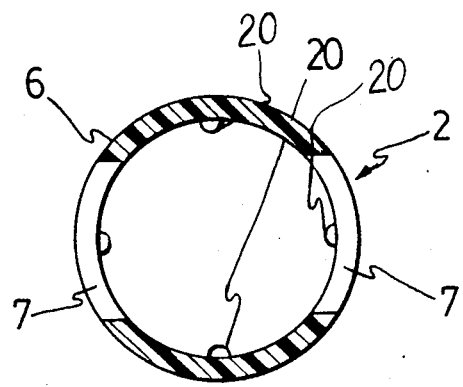
FIG. 2 is a plan view of an outer tubular body portion of the optical apparatus of FIG. 1 in section II—II of FIG. 1.

The outer telescopic body 2 has, at one, free end a cylindrical expansion or mouth with two radial windows 7 in diametrical opposition, as can be more clearly seen in FIG. 2. The windows 7 provide for inserting and positioning a slide (not shown) on which saliva drops to be analyzed have been previously laid.

The inner tubular body 1 with its lenses 3, 4 and 5 can telescopically move axially with respect to the outer tubular body 2 in order to focus the lens system at the opposite, eyepiece, free end of the correctly on the saliva on the slide. This is done by relatively rotating the inner and outer tubular bodies 1, 2, because these are interconnected at threaded zone 8.

The expanded zone 6 of the outer tubular body 2 is provided with an externally-cut threaded end for connection to one, open, threaded end of another tubular body 9 by a threaded ring 10. The opposite end of the other tubular body 9 includes a bottom wall 11 to keep inside it a battery 12 and a bulb 13 for achieving perfect lighting of the slide and, thereby, obtaining a clear view of the focused, saliva image at the opposite, eyepiece end of the inner tubular body 1.

Figure 3:
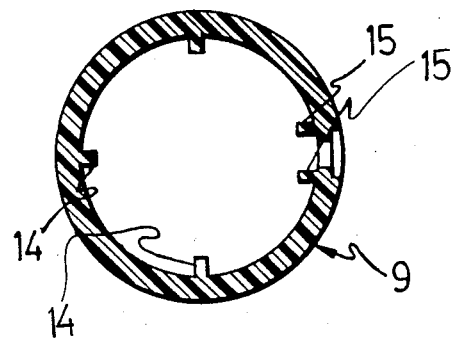
FIG. 3 is a bottom view of another tubular body portion of the optical apparatus of FIG. 1 in section III—III of FIG. 1.

As can be seen from FIGS. 1 and 3 a 1.5 V battery 12 is perfectly guided in the other tubular body 9, because the inner surface of the latter is provided with circumferentially spaced longitudinal ribs 14 and 15. The latter ribs 15 are also used for giving a perfect guide to a conductive plate 16 and related electrical switch, 17 which can establish contact between the poles of the battery 12 through the bulb 13.

When this electrical circuit is so closed, the bulb 13 and a reflecting screen 18 associated therewith send the light from the bulb 13 to the lower side of the slide (not shown) through a diffusing glass 19. One side of the diffusing glass 19 is applied against swellings 20 in the inner periphery of the expansion 6 of the outer tubular body 2 and the diffusing glass 19 fixed thereon with a fastening ring 21 on the opposite side of the diffusing glass 19.

The other, end tubular body 9 and its related electrical elements constitute an assembled light unit. The rest of the optical apparatus, across the connection ring 10, defines a simple, preferably 100-fold magnifying microscope, almost pre-focused on the slide.

All the pieces constituting the optical apparatus, with the exception of the conductive plate 16, are made from a plastic and, therefore, insulating material, including the lens system, which is made from methacrylate, so as to decrease the cost of the unit without detriment to the required optical characteristics.

Figure 4:
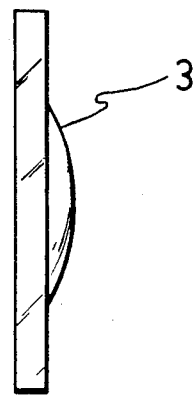
FIGS. 4 to 6 are respective side views of magnifying lens portions of an inner tubular body of the optical apparatus of FIG. 1.
Figure 5:
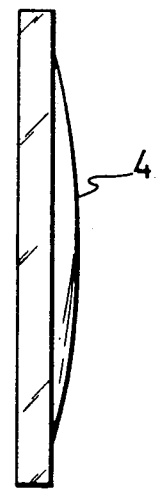
Figure 6:
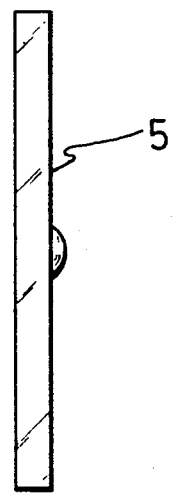

As can be clearly seen in FIG. 1, the lens 4, the geometry of which can be seen in detail in FIG. 5, stands applied against an annular, step site about the inner periphery of the inner telescopic tubular body 1. It is duly fastened thereagainst by an annular piece 22, inserted in the inner mouth of said body 1, the annular piece 22 acting, in its turn, as separating element for the lens 3 (see FIG. 4). The lens 3 is welded to the former with the help of a retaining annular element 23. The other lens 5 (see FIG. 6) stands applied against an annular, step-cut surface of the bottom end of the inner tubular body 1 and so retained by a ring 24.

In order to make the focusing easier, the outer periphery of the upper portion of the inner tubular body 1 is provided with an annular expansion 24, which is grooved or knurled for a better grip thereon. Also, the outer periphery of the connection ring 10 has a grooved or knurled pattern 25 to make assembling and disassembling easier.

I claim:

1. In a system for detecting a fertile period during a woman's menstrual cycle from observation of her saliva with an optical apparatus, an improved optical apparatus, comprising:

an outer tubular body having, at one end, slide-receiving means for receiving a slide, whereby the slide may carry a woman's saliva for an observation, and a diffusing glass for transmitting light to one side of the slide during the observation and, at the opposite end, threads;

an inner tubular body having a lens system of about 100-fold magnification fixed therein, the inner tubular body being telescopically in the outer tubular body and threaded to the threads thereof for axial movement relative thereto upon relative rotation thereof, whereby to focus the lens system on the saliva on the slide for the observation thereof;

another tubular body having an open end and an opposite closed end, whereby to hold a battery, a bulb in the open end, and switch means for lighting the bulb with the battery; and connecting means for connecting the one end of the outer tubular body to the open end of the other tubular body, whereby to provide the light from the bulb to the diffusing glass, slide and lens system for the observation.

* * * * *